United States Patent [19]
Stout

[11] Patent Number: 5,456,701
[45] Date of Patent: Oct. 10, 1995

[54] THERAPY MEMBER INCLUDING INTERNAL BLADDER WITH SURROUNDING PLIABLE GEL

[75] Inventor: Edward I. Stout, Overland Park, Kans.

[73] Assignee: Southwest Technologies, Inc., Kansas City, Mo.

[21] Appl. No.: 201,663

[22] Filed: Feb. 25, 1994

[51] Int. Cl.⁶ .................................................. A61F 7/00
[52] U.S. Cl. ........................ 607/104; 607/107; 607/108; 165/46
[58] Field of Search .................................... 607/104, 107, 607/108–114; 62/536; 383/901; 165/46

[56] References Cited

U.S. PATENT DOCUMENTS

| | | | |
|---|---|---|---|
| 3,830,676 | 8/1974 | Elkins | 607/104 |
| 4,756,311 | 7/1988 | Francis, Jr. | 607/114 |
| 4,846,176 | 7/1989 | Golden | 607/104 |
| 5,034,006 | 7/1991 | Hosoda et al. | 607/104 |
| 5,165,402 | 11/1992 | McCoy | 607/114 |
| 5,230,335 | 7/1993 | Johnson, Jr. et al. | 607/104 |
| 5,241,951 | 9/1993 | Mason et al. | 607/104 |

*Primary Examiner*—Lee S. Cohen
*Assistant Examiner*—Robert L. Nasser, Jr.
*Attorney, Agent, or Firm*—Hovey, Williams, Timmons & Collins

[57] ABSTRACT

An improved therapy member (10) for treatment of sprains, muscle aches and orthopaedic injuries is provided which is very flexible to permit the member to be placed in conforming relationship with a patient's limb or other body part, while also allowing effective hot or cold thermal therapy. The therapy member (10) preferably includes an internal bladder (12) having a fluid inlet (26) and a fluid outlet (28). The bladder (12) is substantially surrounded by a body of flexible, thermally conductive gel (32), the latter being encased within a flexible fabric-type sheath (34). An inlet/outlet fluid supply tubing assembly (16) is coupled with the bladder (12) in order to permit circulation of hot or cold fluid through the bladder (12) for therapy purposes. The gel (32) advantageously includes a water soluble humectant entrapped within a polyacrylamide matrix.

14 Claims, 1 Drawing Sheet

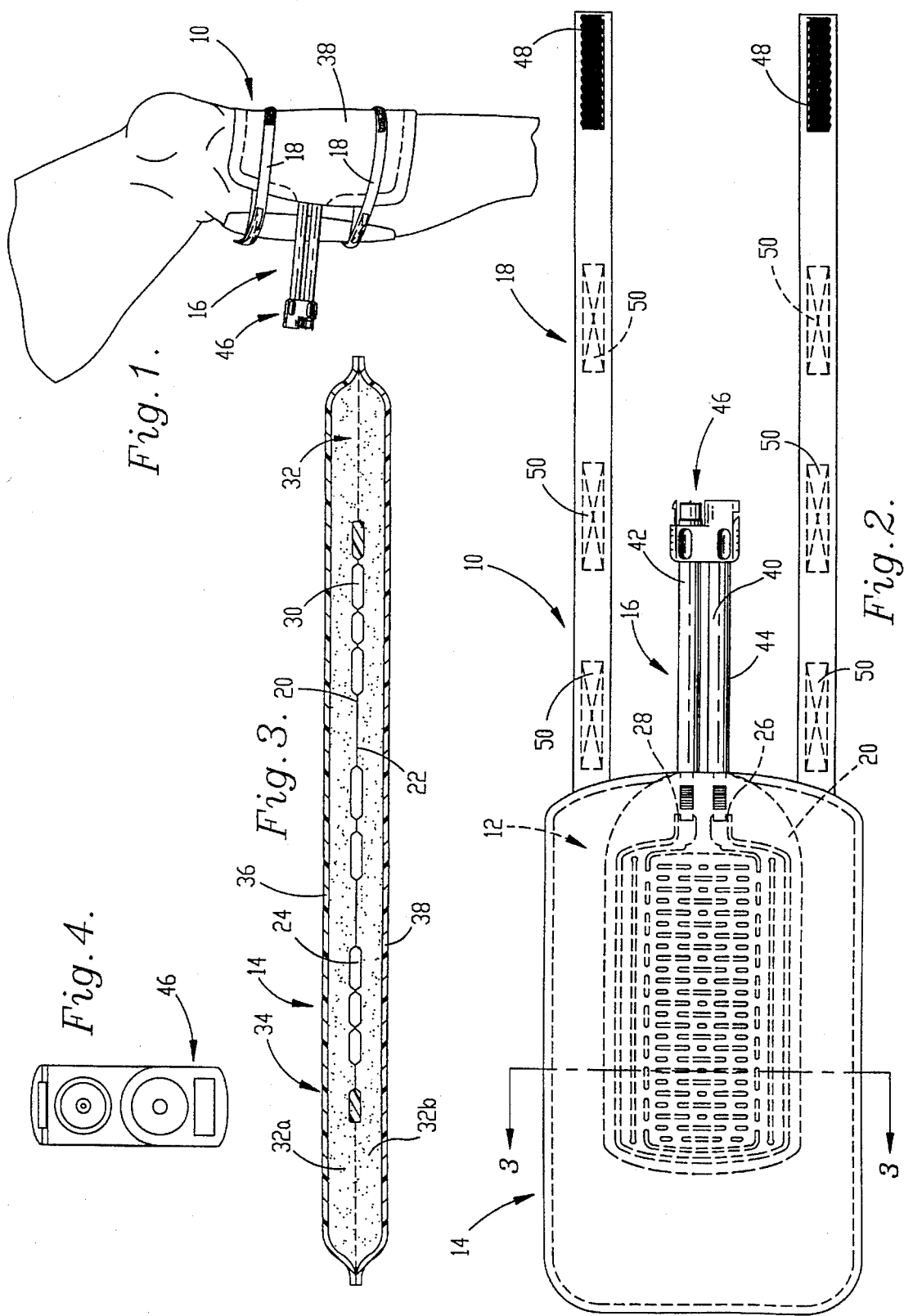

THERAPY MEMBER INCLUDING INTERNAL BLADDER WITH SURROUNDING PLIABLE GEL

BACKGROUND OF THE INVENTION

1. Field of the Invention

The present invention is broadly concerned with an improved bladder-type therapy member designed for use in the treatment of sprains, muscle aches, dislocations, etc. where application of heat or reduced temperatures is advantageous. More particularly, the invention pertains to such therapy members including an internal bladder surrounded by a quantity of flexible, thermally conductive gel; the gel is normally encased within a stretchable fabric sheath, permitting the therapy member to be placed in direct conforming relationship with the body part of a patient requiring therapy.

2. Description of the Prior Art

The treatment of many injuries such as sprains, contusions or dislocations where immediate swelling is common typically involves application of cold ice compresses or other materials to slow the flow of blood to the injured site, thus reducing swelling. After the initial trauma and swelling due to the injury have subsided, it is often advisable to apply heat to the injured area to promote healing. Here again, a number of expedients have been used in the past for this purpose, including hot towels or heating pads.

U.S. Pat. No. 4,671,267 describes a greatly improved gel-based therapy member which can be employed to good effect in the treatment of various traumatic injuries. The therapy members disclosed in the '267 patent make use of a humectant-based gel encased within flexible stretch-type fabric. In use, the therapy members are either cooled in a refrigerator or freezer, or heated by microwave or other heating means. While devices described in this patent represent a significant breakthrough in the art, they do not provide any means for maintaining an initial temperature over long periods. That is to say, while these therapy members may be initially heated or cooled prior to application, once in place the temperature thereof inevitably moves towards ambient.

It has also been known in the past to provide hot/cold blankets for the treatment of post-surgical and traumatic conditions. Generally speaking, such blankets include an internal bladder for receipt of hot or cold fluid, with a plastic skin-contacting sheet of limited flexibility adjacent one face of the bladder, and a sheet of foam adjacent the opposite bladder face. Blankets of this type are commercialized by InCare Medical Products of Libertyville, Ill. under the designation "Hot/Ice System Blanket", and are designed for use with automated equipment for precise temperature maintenance.

These bladder type devices are deficient in that their relatively rigid construction prevents wrapping of the devices around a leg or arm, for example. Thus, these blankets are most useful only for treatment of the trunk regions of recumbent patients.

SUMMARY OF THE INVENTION

The present invention overcomes the problems outlined above, and includes a greatly improved therapy member having an internal bladder surrounded by a quantity of flexible, thermally conductive gel, with means coupled to the bladder for circulation of hot or cold fluids through the bladder. The therapy members hereof are extremely flexible and can be readily wrapped about the limb of a patient for example, so as to give the most effective thermal therapy. At the same time, use of the preferred gels enhances the therapeutic effect because the gels have excellent thermal conductivity characteristics.

In more detail, the therapy members of the invention include an internal bladder including wall structure defining a cavity, with an inlet and outlet in communication with the cavity. A sheath assembly including a quantity of flexible, thermally conductive gel surrounds the bladder. In preferred forms, the sheath assembly includes a pair of interconnected sheets of flexible material. The therapy member further includes means coupled with the inlet and outlet of the bladder for circulation of fluid through the bladder cavity in order to alter or maintain the temperature of the therapy member.

The preferred gel material includes a water soluble humectant such as glycerin entrapped within a polymeric matrix having therein acrylic acid or acrylamide monomer moieties; the thickness of the gel material should range from about ⅛–1 inch, and more preferably from about ¼–½ inch.

The overall therapy member also advantageously includes strap means for releasably maintaining the therapy member in a conforming relationship to the body part of a patient. Additionally, inlet and outlet tubes are preferably coupled with the bladder inlet and outlet respectively, so as to permit ready connection with inlet and outlet fluid supply lines.

BRIEF DESCRIPTION OF THE DRAWINGS

FIG. 1 is a perspective view illustrating a therapy member in accordance with the invention applied to the calf region of a patient;

FIG. 2 is a plan view of the preferred therapy member illustrated in FIG. 1;

FIG. 3 is a sectional view taken along line 3—3 of FIG. 2 and illustrating the internal construction of the therapy member; and FIG. 4 is an end view illustrating the line coupling head attached to the inlet and outlet tubes of the therapy member.

DETAILED DESCRIPTION OF THE PREFERRED EMBODIMENTS

Turning now to the drawings, and particularly FIG. 2, a therapy member 10 is depicted. Broadly speaking, the therapy member 10 includes an internal bladder 12 surrounded by a sheath assembly 14. An inlet/outlet fluid tube assembly 16 is operatively coupled with internal bladder 12, and flexible straps 18 are attached to the sheath assembly 14.

In more detail, the internal bladder 12 is formed of flexible synthetic resin material and includes interconnected top and bottom panels 20, 22 which define a segmented internal cavity 24, as well as a fluid inlet 26 and a fluid outlet 28. As best seen in FIG. 2, the panels 20, 22 are connected so as to define a tortuous flow path for fluid from inlet 26 to outlet 28. This flow path is further illustrated in FIG. 3, where it will be seen that incoming fluid is directed through a series of elongated, interconnected channels 30 which cooperatively define the overall internal cavity 24. Of course, the particular configuration of cavity 24 is not crucial to the invention, except to the extent that the configuration maximizes the thermal transfer capacity of the therapy member. Accordingly, as used herein, the term "bladder" should be understood in a broad sense, and is intended to embrace all types of fluid-conveying structures (e.g., tubing sections) which can function in accordance with the principles of the invention.

Sheath assembly 14 includes a quantity of flexible, thermally conductive gel 32 which substantially surrounds bladder 12. In the form illustrated, the gel 32 includes a pair of gel sheets 32a, 32b respectively placed in contact with the bladder-defining panels 20, 22. These sheets effectively form a coherent body of gel, inasmuch as they are sticky and adhere both to the bladder and to themselves. The total thickness of the gel portion of the assembly 14 should range from about ⅛–1 inch, and more preferably from about ¼–½ inch. In practice, a total gel thickness of about ⅜ inch has been found to be suitable.

The preferred gel 32 includes a water soluble humectant entrapped within a polymeric matrix. Such materials are described in U.S. Pat. No. 4,671,267 incorporated by reference herein.

While a wide variety of formulations can be employed to good effect in the context of the invention, it has been found that certain specific components and ranges give the most satisfactory results. For example, the polymeric matrix is most preferably formed of acrylamide, whereas the humectant is in the form of glycerin. Other components, such as methylene-bisacrylamide cross-linking agent, ammonium persulfate initiator and citric acid are also employed in such preferred formulations.

The following table sets forth the most preferred formulations, as well as desirable approximate ranges of use for the respective constituents, both in the case of the therapy wraps and skin dressings:

TABLE 1

| Constituent | [1]Therapy Wrap Preferred | Range | [1]Skin Dressing Preferred | Range |
| --- | --- | --- | --- | --- |
| Citric Acid | 0.02% | 0.01–0.10 | 0.02 | 0.01–0.10 |
| Ammonium persulfate | 0.04 | 0.01–0.2 | 0.04 | 0.02–0.15 |
| N,N methylene-bisacrylamide | 0.09 | 0.04–0.2 | 0.08 | 0.02–0.15 |
| [2]Acrylamide | 17.97 | 10.0–30.0 | 14.42 | 10.0–25.0 |
| [2]Water | 17.97 | 10.0–80.0 | 14.42 | 10.0–50.0 |
| Glycerin | 63.91 | 20.0–85.0 | 71.00 | 50.0–85.0 |
| 3Super absorbant | — | — | 0.02 | 0.10–0.60 |

[1]All data in percentages by weight
[2]Premixed as a 50% by weight solution of acrylamide and water
[3]Hydrolyzed starch-acrylonitrile graft copolymer (an optional ingredient)

In fabricating the gel bodies using the above constituents, it is desirable to admix and stir all of the constituent materials at a temperature of above about 65° F., whereupon the liquid mixture is into an appropriate old and allowed to set for a period of a least about ½ hour to 45 minutes, and more preferably for about 24 hours. At the end of the time, the gel can be cut to an appropriate size and configuration.

While the above table sets forth the preferred constituents and ranges, those skilled in the art will appreciate that the invention is not so limited. For example, while the preferred crosslinking agent is N,N methylene-bisacrylamide (MBA), other types of crosslinking agents can be employed such as N-methylolacrylamide, allyl methacrylate, and ethylene glycol dimethacrylate. Moreover, while ammonium persulfate is a suitable initiator for the polymerization reaction, the use of an initiator is not essential. Finally, while acrylamide is the preferred matrix-forming material, other similar materials can also be used, such as acrylic acid. In such cases, the acrylic acid should be used at a level of from about 10–20% by weight, humectant at a level of from about 20–80% by weight, water at a level of from about 20–70% by weight, MBA at a level of from about 0.01–0.04% by weight. The most preferred ranges are from about 14–18% acrylic acid, from about 50–76% humectant, from about 8–22% water, and from about 0.02–0.3% crosslinking agent.

Those skilled in the art will also appreciate that by proper selection of monomer and by varying the ratio of monomer (or monomers) relative to the crosslinking agent and humectant, the hardness and toughness of the gel material may be altered and controlled.

The overall sheath assembly 14 further includes a flexible fabric-type sheath 34 surrounding the gel 32. The sheath 34 is preferably made from a pair of interconnected flexible sheets 36, 38. The sheet 36 is adapted for contacting a patient's skin, and is preferably formed of Darlexx stretch fabric having the internal face thereof adjacent gel 32 coated with a polyurethane. The Darlexx material is described in U.S. Pat. No. 4,761,324, which is incorporated by reference herein. The opposed sheet 38 is preferably formed of Rubatex R-1400-N neoprene fabric sold by the Rubatex Corporation of Redford, Va. The physical properties of this material are set forth in a technical data sheet entitled "Rubatex Stock Physical Properties"; this data sheet is incorporated by reference herein.

As best illustrated in FIG. 2, the inlet/outlet tube assembly 16 passes through the interconnected flexible sheets 36, 38 and is coupled with the inlet and outlet 26, 28 of bladder 12. The assembly 16 includes a pair of adjacent tubes 40, 42 encased within a surrounding, resilient rubber-like protector 44. The inner tubes of the 40, 42 are coupled to the corresponding inlet and outlet of the bladder 12. The outboard end of the assembly 16 is in the form of a coupler 46 permitting the ready attachment and detachment of fluid inlet and outlet lines (not shown).

A pair of attachment straps 18 are sewn to the fabric sheath 34 on opposite sides of the assembly 16. Each of these straps 18 is formed of stretch fabric material and includes a terminal Velcro pad 48 on one face thereof. In addition, three mating Velcro pads 50 are attached to the opposite face of each strap at spaced locations between terminal pad 48 and the fabric sheath 34.

Attention is next directed to FIG. 1 which illustrates the therapy member 10 operatively secured to the calf of a patient. As illustrated, the member 10 is wrapped around the patient's calf region with sheet 36 in contact with the patient's skin. The flexible therapy member is maintained in this position by means of the straps 18 which are wrapped around the therapy member and attached together via the mating Velcro pads 50 thereof. The tube assembly 16 extends outwardly from the main body of the member 10, so as to permit attachment of inlet and outlet fluid supply lines carrying thermal fluid such as hot or cold water. When such supply lines are attached via coupler 46, treatment fluid passes through tube 40 and into internal bladder 12 where it traverses the tortuous flow path within the latter. This fluid then exits through outlet 28 and tube 42 to complete the circulation path.

As can be appreciated, use of the therapy member 10 serves to alter and/or maintain the temperature of the therapy member, thus giving the desired thermal therapy to the patient. Moreover, use of the flexible, thermally conductive gel 32 enhances this desirable result.

I claim:

1. A therapy member consisting essentially of:
an outer sheath including walls defining an interior chamber;

a quantity of flexible, thermally conductive gel within said interior chamber;

an inner bladder consisting essentially of walls formed of flexible synthetic resin material and defining an internal cavity and an inlet and outlet in fluid communication with said cavity, wherein said bladder is positioned entirely within said interior chamber with said conductive gel entirely surrounding and in direct contact with said bladder walls; and means operatively coupled with said inlet and said outlet for circulation of fluid through said cavity to alter or maintain a temperature of the therapy member.

2. The therapy member of claim 1, said bladder including internal structure within said cavity for defining a tortuous fluid flow path from said inlet to said outlet.

3. The therapy member of claim 1, including a flexible sheath surrounding said quantity of gel.

4. The therapy member of claim 3, said sheath including a pair of interconnected sheets of flexible material.

5. The therapy member of claim 4, one of said sheets being adapted for contact with human skin and comprising a stretch fabric having a face thereof adjacent said gel coated with polyurethane.

6. The therapy member of claim 5, the other of said sheets being formed of neoprene.

7. The therapy member of claim 1, said gel including a water soluble humectant entrapped within a polymeric matrix having therein acrylic acid or acrylamide monomer moieties.

8. The therapy member of claim 7, said humectant being selected from the group consisting of glycerin, ethylene glycol, propylene glycol, dimethyl sulfoxide and dimethyl formamide.

9. The therapy member of claim 7, said matrix comprising from about 10–30% by weight of polymers of said acrylic acid or acrylamide monomer moieties.

10. The therapy member of claim 1, said gel being characterized by the properties of maintaining pliability over a temperature range of from about 20°–350° F.

11. The therapy member of claim 1, said gel having a total thickness of from about ⅛–½ inch.

12. The therapy member of claim 11, said thickness being from about ¼–½ inch.

13. The therapy member of claim 1, said circulation means comprising an inlet tube and outlet tube operatively coupled with said inlet and outlet respectively and including means for connection thereto of inlet and outlet fluid supply lines.

14. The therapy member of claim 1, including strap means for releasably maintaining said therapy member in conforming relationship with a body part of a patient.

* * * * *